United States Patent [19]

Kirst

[11] 4,205,164
[45] May 27, 1980

[54] ANTIBIOTIC A201C, A201D AND A201E

[75] Inventor: Herbert A. Kirst, Indianapolis, Ind.

[73] Assignee: Eli Lilly and Company, Indianapolis, Ind.

[21] Appl. No.: 17,018

[22] Filed: Mar. 2, 1979

[51] Int. Cl.$^2$ .................................... C07D 405/14
[52] U.S. Cl. ................................. 542/421; 424/119; 536/4; 536/26; 542/422
[58] Field of Search ................ 424/119; 542/421, 422; 536/26

[56] References Cited

U.S. PATENT DOCUMENTS

| | | | |
|---|---|---|---|
| 3,843,784 | 10/1974 | Hamill et al. | 424/119 |
| 4,087,603 | 5/1978 | Hamill et al. | 536/26 |
| 4,143,141 | 3/1979 | Ensminger | 424/119 |

OTHER PUBLICATIONS

Kirst et al., Abstracts of 16th Interscience Conference on Antimicrobial Agents & Chemotherapy, Oct. 27–29, 1976, paper #61.

Primary Examiner—Arthur P. Demers
Attorney, Agent, or Firm—David E. Frankhouser; Arthur R. Whale

[57] ABSTRACT

Antibiotics of the formula

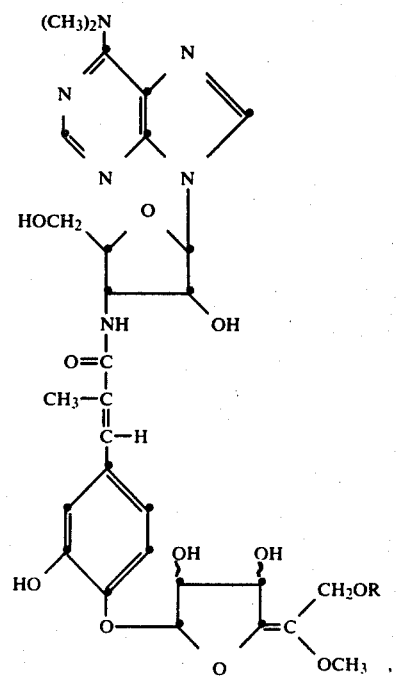

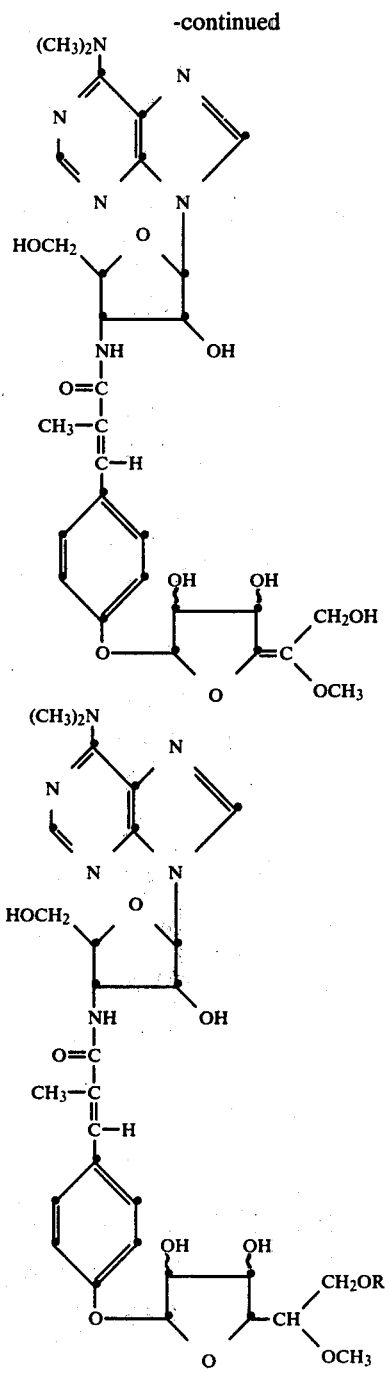

wherein R is α-3,4-di-O-methylrhamnosyl, are produced by the cultivation of *Streptomyces capreolus* NRRL 11429 under submerged aerobic fermentation conditions. A crude antibiotic mixture is obtained from the fermentation medium by extraction. The compounds of Formula II, III, and IV are separated from coproduced Antibiotic A201A (See U.S. Pat. No. 3,843,784) and from each other by repetitive chromatography on silica gel.

3 Claims, No Drawings

ANTIBIOTIC A201C, A201D AND A201E

Antibiotic A201A, which is produced by culturing the organism *Streptomyces capreolus* NRRL 3817, is described in U.S. Pat. No. 3,843,784. The structural formula of Antibiotic A201A, as disclosed by H. Kirst et al., *Abstracts of 16th Interscience Conference on Antimicrobial Agents and Chemotherapy*, Paper No. 61, Chicago, Ill., Oct. 27–29, 1976, is shown below in Formula I:

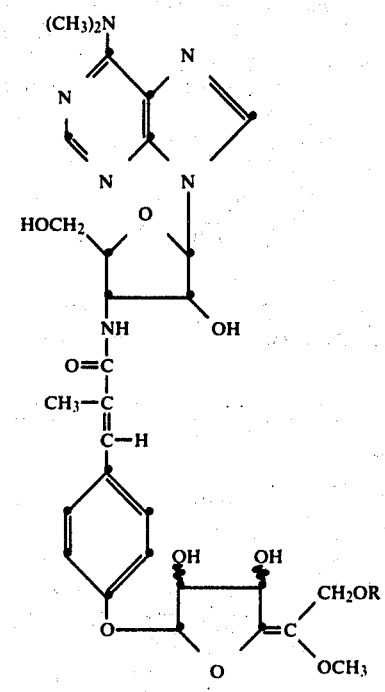

where R is α-3,4-di-O-methylrhamnosyl.

The present invention comprises new antibiotic compounds related to Antibiotic A201A, which compounds have the formulae:

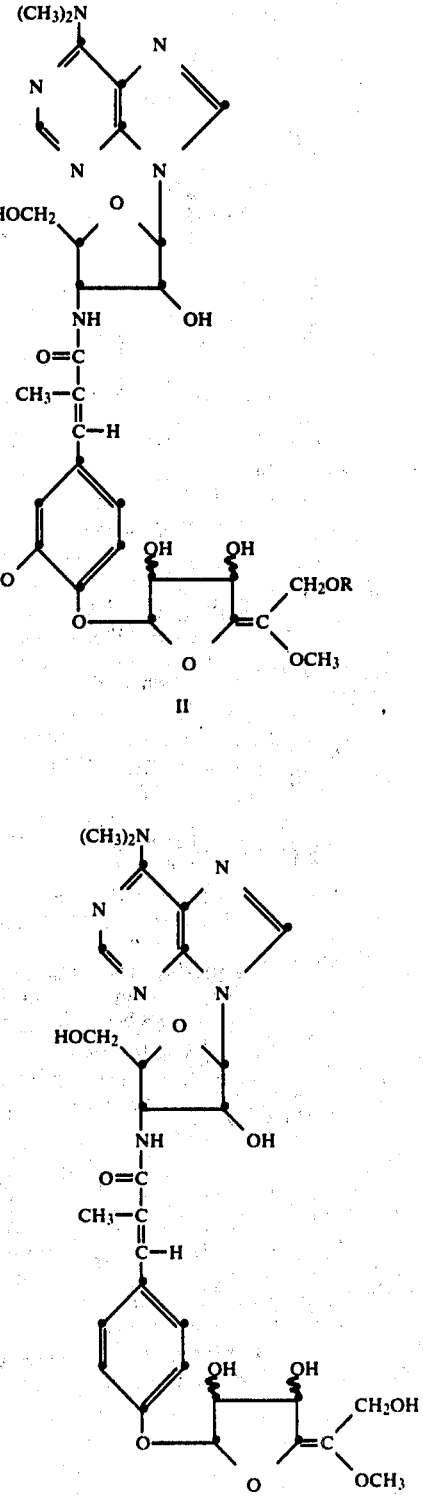

III and

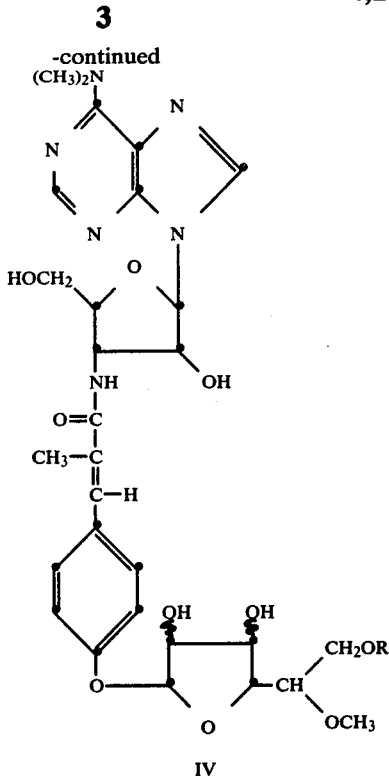

IV wherein R is α-3,4-di-O-methylrhamnosyl.

The compounds of the invention (i.e. the compounds of Formula II, III, and IV) inhibit the growth of certain pathogenic microorganisms, particularly Gram positive bacteria. The compound of Formula II has shown *in vivo* therapeutic activity against experimental bacterial infections in mice.

The compounds of formula II, III, and IV are coproduced in very small amounts with Antibiotic A201A by culturing Streptomyces capreolus NRRL 11429 under submerged aerobic fermentation conditions as described hereinafter in Example 1. For convenience, the compounds of Formula II, III, and IV will be identified herein as follows:

Compound II: Antibiotic A201C or A201, Factor C;
Compound III: Antibiotic A201D or A201, Factor D;
Compound IV: Antibiotic A201E or A201, Factor E;

Streptomyces capreolus NRRL 11429 is a natural variant of *Streptomyces capreolus* NRRL 3817, the cultivation and detailed description of which are disclosed in U.S. Pat. No. 3,843,784, the entire disclosure of which is incorporated herein by reference. The actinomycete used in accordance with this invention for the production of Antibiotics A201C, A201D, and A201E has been deposited without restriction as to availability with the permanent culture collection of the Northern Utilization Research and Development Laboratory, Agriculture Research Service, United States Department of Agriculture, Peoria, Ill., and has been assigned the accession number NRRL 11429.

Antibiotics A201C, A201D, and A201E can be recovered and isolated from the culture medium by methods which are conventional in the fermentation arts, such as filtration, solvent extraction, and chromatography. The preferred method for isolating A201C, A201D, and A201E from the culture medium is illustrated herein in Examples 2, 3, and 4. In this method, the fermentation broth is filtered, and the filtrate, after adjustment of the pH to 8.5, is extracted with a conventional water-miscible solvent (e.g. chloroform). After extraction, the solvent is evaporated to afford a dry residue which is dissolved in methanol and filtered. The methanol solution is taken to dryness under vacuum, and the residue so obtained is dissolved in chloroform. The chloroform solution is then added to a large volume of petroleum ether which results in precipitation of the antibiotic substances. The precipitate is dried under vacuum to give a crude product which comprises A201A and the minor factors coproduced in the fermentation.

The minor factors are isolated and recovered from the crude product according to the following procedure:

The crude product is first subjected to a chromatographic separation on silica gel. This is accomplished by dissolving the crude product in acetone and adding the solution so obtained to the silica gel column packed in 1:1 chloroform-acetone. The column is then eluted with 1:1 chloroform-acetone and then with acetone. Fractions are collected. Each fraction is bioassayed and analyzed by thin layer chromatography (tlc) for the presence of A201A and other factors. The fractions containing A201A and more polar factors are pooled. The solvent is removed to give an oil which is subjected to repetitive chromatography (See Example 4) on silica gel to yield the individual factors (A201C, A201D, and A201E).

In order to obtain sufficient amounts of Factors C, D, and E for isolation and identification, pooled fractions from many separate chromatographic separations can be combined. In Example 4 herein, pooled fractions obtained from seven initial separations (from a total of about 2102 grams of crude fermentation product) are employed to produce the oil used for the repetitive chromatography which yields A201C, A201D, A201E.

EXAMPLE 1

TANK FERMENTATION

Spores of Streptomyces capreolus, NRRL 11429 are inoculated on a nutrient agar slant having the following composition:

| Ingredient | Amount |
|---|---|
| Oatmeal | 60.0 g. |
| Yeast | 2.5 g. |
| K$_2$HPO$_4$ | 1.0 g. |
| Czapek's mineral stock solution* | 5.0 ml. |
| Agar | 25.0 g. |
| Water, distilled, q.s. to | 1 l. |

*Prepared frm KCL, 100 g.; MgSO$_4$ . 7H$_2$O, 100 g.; FeSO$_4$ . 7H$_2$O, 2 g. (dissolved in 2 ml. conc. HCl); and distilled water, q.s. to 100 ml.

Before sterilization, the pH of the growth medium is adjusted to 7.3 with 5 N potassium hydroxide. The pH of the medium after sterilization is 6.7.

The inoculated slant is incubated at about 34° C. for about 7 days, and then a small amount of sterile distilled water is added and the surface of the agar is scraped gently with a sterile platinum wire loop to loosen the organism and obtain an aqueous suspension.

One-half ml. of the suspension so obtained is used to inoculate 50 ml. of a sterile vegetative growth medium having the following composition:

| Ingredient | Amount |
| --- | --- |
| Dextrose | 15 g. |
| Bactopeptone | 10 g. |
| Glycerol | 10 g. |
| Amber ALB[1] | 10 g. |
| Blackstrap Molasses | 5 g. |
| Nadrisol[2] | 10 g. |
| Water, distilled q.s. | 1 l. |

[1]Amber ALB is a tradename designation for a milk-albumin product of Amber Laboratories, Juneau, Wisconsin 55039.
Nadrisol is a tradename designation for a corn distiller's dried solubles produt of National Distillers Products Company, New York.

The pH of this growth medium is adjusted to 7.0–7.2 with 5 N sodium hydroxide before sterilization. The pH of the medium is 6.5–6.6 after sterilization. The inoculated vegetative growth medium is incubated for 48 hours at about 30° C. with constant agitation on a rotary shaker operating at 250 rpm.

Vegetative culture prepared as described above is conveniently maintained in liquid nitrogen by the following procedure:

In a small (13-×100-mm) sterilized screwcap tube is placed 2 ml of a suspension agent having the following composition:

| Ingredient | Amount |
| --- | --- |
| Glycerol | 20% |
| Lactose | 10% |
| Water (deionized) | 70% |

To this suspension agent is added a 2-ml sample of the 48-hour-incubated vegetative medium prepared as above-described. The mixed solution is frozen and maintained in the gas phase of a liquid-nitrogen tank.

Vegetative culture thus stored is thawed for use in tank fermentation by placing the vial in a 43° C. water bath. A portion of the thawed solution (1 ml) in the vial is used to inoculate each of two 250-ml. flasks containing 55 ml. of a first-stage vegetative growth medium having the same composition as that described above. The inoculated medium is incubated for 48 hours at about 30° C. with constant agitation on a rotary shaker operated at 250 rpm. A 15 ml portion of the culture is used to inoculate each of two 2 l. flasks containing 660 ml. of a second-stage vegetative growth medium also having the same composition as that described above. The inoculated second-stage medium is allowed to ferment under the same conditions employed for the first-stage medium.

A 1% inoculum of the second-stage culture is used to inoculate 100 l. of the following medium in a 165 l. tank fermentation:

| Ingredient | Amount |
| --- | --- |
| Blackstrap molasses | 300 g. |
| CaCO$_3$ | 250 g. |
| K$_2$HPO$_4$ | 20 g. |
| Amber EHC[1] | 1000 g. |
| Cotton seed oil | 5000 ml. |
| Methyl oleate | 1500 ml. |
| Antifoam A[2] | 20 g. |

[1]Amber EHC is a trademark designation for a enzyme-hydrolyzed casein product of Amber Laboratories, Juneau, Wisconsin.
[2]Dow-Corning The pH of the medium is 7.6 after sterilization. The inoculated medium is aerated at a rate of 0.25 volume of air per volume of culture per minute and is stirred with conventional agitation at 250 rpm. The fermentation is carried out for about six days.

EXAMPLE 2

Isolation of Crude Product from Fermentation Broth

The fermentation broth obtained as described in Example 1 is filtered in the presence of a filter aid (3–4%; Hyflo), and the filtrate is adjusted to pH 8.5 with 5 N sodium hydroxide. The alkaline filtrate is extracted once with 1 volume of chloroform. The chloroform solvent is removed by evaporation, and the resulting residue is dissolved in methanol (about 500 ml). Insolubles are removed by filtration and discarded. The methanol filtrate is evaporated to dryness under vacuum, and the residue thus obtained is dissolved in chloroform (about 500 ml). The solution is added to 20 volumes of petroleum ether and a precipitate forms. The precipitate is removed and dried under vacuum to give a crude product.

EXAMPLE 3

Initial Chromatography of Crude Product

The crude fermentation product obtained as described in Example 2 is dissolved in chloroform (about 1.5 to 2 L.). A 16-L. chromatographic column is prepared using silica gel (Grace 62, Davison Chemical Co) slurried in a mixture of 1:1 chloroform-acetone. The excess vehicle is drained away as the silica gel settles and the chloroform solution containing the crude fermentation product is loaded onto the column. The column is then eluted with 5 column volumes of a 1:1 chloroform-acetone mixture and then with 5 column volumes of acetone. Fractions each containing 4 L. of solution are collected. Each fraction is tested for antibiotic activity (using *Bacillus subtilis*) and is analyzed by thin layer chromatography.

After the main fractions containing pure Antibiotic A201A are eluted, fractions containing Antibiotic A201A and minor, more polar factors are eluted, as shown by thin layer chromatography of each fraction. The tlc plates are developed two or three times in a solvent system of either 6:1 (v:v) chloroform-ethanol or 6:1 ethyl acetate-ethanol. The minor factors are best detected by scanning the tlc plate on a Schoeffel 3000 thin layer scanning densitometer at a wavelength of about 275 nm. The fractions containing both Antibiotic A201A and the more polar factors are pooled.

EXAMPLE 4

Repetitive Chromatography: Isolation of Antibiotic A201C, A201D, and A201E (1) A201 Factor C Pooled fractions obtained as in Example 3, from seven distinct chromatographic separations of crude fermentation products (from a total of 2102 g. of crude product) are combined, and the solvent is evaporated under reduced pressure. A residue of dark brown oil (125 g) is obtained. A 34.8 g. sample of this oil dissolved in 5% ethanol-ethyl acetate is loaded on a silica gel column (Grace 62) and eluted with 5% ethanol-ethyl acetate and then with 6% ethanolethyl acetate. Fractions which are collected are monitored by TLC (as described in Example 3) for the presence of Antibiotic A201A and coproduced factors. Elution with 6% ethanol-ethyl acetate initially gives fractions containing only A201A and A201C (2.3 g). Continued step-wise elution with 6%, 8%, and 10% ethanol-ethyl acetate yields fractions containing A201A and Factor C along with other factors. Appropriate fractions are pooled on the basis of tlc analysis.

The fraction containing only A201A and A201C is dissolved in 10% ethanol-chloroform and loaded on a prepacked size C silica gel column (E. Merck). The column is eluted with 10% ethanol-chloroform under low pressure (5 psi), and fractions shown to contain predominantly Factor C by tlc analysis are combined to give after removal of solvent 0.2 g. of product. Additional amounts of Factor C are obtained by repeated chromatography on silica gel of the appropriately pooled fractions obtained in the original larger-scale chromatography. Elution with 5-10% ethanol in either chloroform or ethyl acetate gives additional samples of Factor C which are further purified by crystallization from ethyl acetate. The cold mother liquor is decanted and the crystals are triturated with ether, filtered, and dried. An analytical sample is prepared by further crystallization using the above-described technique.

The samples of Factor C described above were shown to be identical by tlc analysis, bioautography and physical chemical data. Factor C has the following physical characteristics: m.p. 135°-137°; TLC: $R_f$ 0.35 (6:1 chloroform-ethanol, two developments, 0.48 for A201A) and $R_f$ 0.19 (6:1 ethyl acetate-ethanol, two developments, 0.31 for A201A); $[\alpha]_D^{25}=-114°$ (c=10 mg/ml, MeOH); $pK_a=11.4$ (66% DMF-H$_2$O); UV max. (95% EtOH): 279 nm ($\epsilon=33,200$), 217 nm ($\epsilon=41,500$) with a shift in basic solution to 325 nm ($\epsilon=14,200$), 268 nm ($\epsilon=44,600$) and end absorption; IR (CHCl$_3$): 3350-3400 (broad, OH), 1640 (amide C=O), 1595 cm$^{-1}$ (aromatic); NMR (dry DMSO-d$_6$): δ8.9 (very broad, 1H, phenolic OH), 6.8-7.1 (multiplet, 3H, aryl) (the rest of the spectrum is very similar to that of A201A); field desorption mass spectrum: m/e 819 (M+1); electron impact mass spectrum (70 eV): highest m/e 470; high resolution measurement: 470.1883 (C$_{22}$H$_{26}$N$_6$O$_6$).

Analysis: Calcd. for C$_{37}$H$_{50}$N$_6$O$_{15}$: C, 54.27; H, 6.16; N, 10.26%. Found: C, 54.06; H, 6.44; N, 9.97%

(2) Factor D

During the chromatographic purification of Factor C, a new factor eluting after A201C is obtained. The material is purified by chromatography on prepacked silica gel columns, (E. Merck) eluting with 5-10% ethanol-chloroform. Crystallization from methanol gives Factor D, m.p. 128°-130°; TLC: $R_f$ 0.29 (6:1 chloroform-ethanol, two developments) and $R_f$ 0.23 (6:1 ethyl acetate-ethanol, two developments); UV max. (95% EtOH): 279 nm ($\epsilon=39,700$) and 213 nm ($\epsilon=40,300$); IR (KBr): 3450-3500 (broad, OH), 1640 (amide C=O), 1600 cm$^{-1}$ (aromatic); NMR (dry DMSO-d$_6$): almost identical to that of A201A except for the absence of the 3,4-di-O-methylrhamnose protons; field desorption mass spectrum: parent m/e 629 (M+1); electron impact mass spectrum (70 eV): highest m/e 454.

(3) Factor E

While examining samples of Factor C by tlc, another factor is found which is poorly separated from Factor C in chloroform-ethanol, but is readily separated using ethyl acetate-ethanol. The new factor is purified by chromatography on prepacked silica gel columns (E. Merck) eluted with 5-10% ethanol in ethyl acetate. This new factor, Factor E, has the following characteristics: TLC: $R_f$ 0.34 (6:1 chloroform-ethanol, 2 developments) and $R_f$ 0.25 (6:1 ethyl acetate-ethanol, 2 developments); UV max. (95% EtOH): 278 nm ($\epsilon=37,400$) and 215 nm ($\epsilon=27,800$); IR (CHCl$_3$): 3400 (broad, OH), 1645 (amide C=O), 1595 cm$^{-1}$ (aromatic); NMR (dry DMSO-d$_6$): very similar to that of A201A in most respects, but the protons assigned to the unsaturated sugar moiety in A201A have generally moved upfield; field desorption mass spectrum:parent m/e 805 (M+1); electron impact mass spectrum (70 eV): highest m/e 454.

The proton nmr spectra of Antibiotic A201 Factor C, Factor D, and Factor E, run in dry DMSO, are tabulated below where chemical shifts are expressed in ppm downfield from internal TMS:

|  | A201A | Factor C | Factor D | Factor E |
|---|---|---|---|---|
| Adenine moiety | | | | |
| H2 | 8.46 | 8.47 | 8.47 | 8.47 |
| H8 | 8.24 | 8.23 | 8.23 | 8.23 |
| CH$_3$ | 3.47 | 3.47 | 3.47 | 3.46 |
| Aminopentose moiety | | | | |
| H1 | 6.05 | 6.04 | 6.04 | 6.04 |
| H2 | 4.56 | 4.55 | 4.58 | 4.55 |
| 2-OH | 5.95 | 5.95 | 5.96 | 5.94 |
| H3 | 4.60 | 4.55 | 4.58 | 4.55 |
| 3-NH | 7.83 | 7.85 | 7.75 | 7.83 |
| H4 | 4.22 | b | 4.24 | 4.24 |
| H5 | 3.59,3.77 | b | 3.6-3.75 | b |
| 5-OH | 5.22 | 5.20 | 5.21 | 5.20 |
| Aromatic acid moiety | | | | |
| CH$_3$ | 2.05 | 2.04 | 2.05 | 2.04 |
| Vinyl | 7.27 | 7.2 | 7.27 | 7.25 |
| H$_2$, H$_6$ | 7.08,7.17 | 6.83,6.90 | 7.07,7.16 | 7.01,7.10 |
| H$_3$,H$_5$ | 7.27,7.36 | 7.09 | 7.36,7.45 | 7.32,7.41 |
| OH | — | 8.9 | — | — |
| Unsaturated | sugar moiety | | | |
| H1 | 5.86 | 5.83 | 5.83 | 5.52 |
| H2 | 4.10 | b | 4.1 | <4.2 |
| 2-OH | 5.57 | b | 5.52 | 5.33 |
| H3 | 4.55 | 4.55 | 4.58 | <4.1 |
| 3-OH | 5.65 | 5.68 | 5.52 | 5.33 |
| 5-OCH$_3$ | 3.49 | 3.51 | 3.51 | 3.19 |
| H6 | 4.01,4.32 | b | 4.06 | b |
| 6-OH | — | — | 4.53 | — |
| Di-O-Methylrhamnose moiety | | | | |
| H1 | 4.68 | 4.68 | — | 4.59 |
| H2 | 3.84 | b | — | b |
| 2-OH | 4.85 | 4.87 | — | 4.87 |
| H3 | 3.22 | 3.19 | — | b |
| 3-OCH$_3$ | 3.29 | 3.30 | — | 3.29 |
| H4 | 3.02 | 3.02 | — | 3.00 |
| 4-OCH$_3$ | 3.40 | 3.40 | — | 3.39 |
| H5 | 3.55 | b | — | b |
| H6 | 1.17 | 1.16 | — | 1.14 | b not assigned

The minimal inhibitory concentrations (MIC's) at which A201C, A201D, and A201E inhibit selected Gram positive bacteria, as determined by standard agar-dilution tests, are summarized in Table I:

Table I

MIC of A201C, A201D, and A201E against Gram positive Bacteria by Agar Dilution Method

| | MIC (μg/ml) | | | | | | | | | | |
|---|---|---|---|---|---|---|---|---|---|---|---|
| | Staph. aureus. | | | Staph. epi. | | streptococcus | | | | H. influ. | |
| Compound | X1.1 | V41 | X400 | Epi1 | Epi2 | C203 | S13E Park | X66 | 9960 | HOLT | R252 |
| Factor C | 8 | >128 | 8 | 8 | 128 | 64 | 1 | 8 | 64 | >128 | 132 | 32 |
| Factor D | 32 | >128 | 64 | 32 | 128 | 128 | 8 | 64 | >128 | >128 | 128 | 64 |
| Factor E | 16 | 128 | 16 | 16 | 64 | 64 | 1 | 16 | 64 | >128 | 32 | 32 |
| A201A | 1 | 16 | 1 | 1 | 16 | 8 | .25 | 4 | 8 | 64 | 8 | 4 |

A201C has shown *in vivo* therapeutic activity against experimental bacterial infections when tested as follows: Mice are given a lethal dose of the infective organism by interperitoneal injection. One hour and five hours later the mice are given a subcutaneous (S.C.) dose of the compound in 60% propylene glycol. The compound is administered at five different dosage levels (eight mice for each dosage level). The animals are observed for 7 days and the number of survivors is noted. For each organism, the ED$_{50}$ value is calculated using the method of W. Wick, *J. Bacteriol.* 81, 233 (1961). The results of the testing of A201C against three representative bacteria are given in Table II:

Table II

Therapy of Mouse Infections with A201C

| Mouse Infections[a] | Dose (mg/kg)[b] | Survivors/Total No. of Mice | ED$_{50}$ (mg/kg × 2) |
|---|---|---|---|
| Streptococcus pyogenes C203 (243 LD$_{50}$'s) | 35 | 8/8 | 5.3 |
| | 17.5 | 8/8 | |
| | 8.75 | 6/8 | |
| | 4.375 | 4/8 | |
| | 2.19 | 0/8 | |
| Staphylococcus aureus 3055 (260 LD$_{50}$'s) | 35 | 5/8 | 26.0 |
| | 17.5 | 0/8 | |
| | 8.75 | 3/8 | |
| | 4.375 | 1/8 | |
| | 2.19 | 0/8 | |
| Diplococcus pneumoniae Park I (260 LD$_{50}$'s) | 70 | 0/8 | >70 |
| | 35 | 0/8 | |
| | 17.5 | 0/8 | |
| | 8.75 | 0/8 | |
| | 4.378 | 0/8 | |

[a]Administered IP.
[b]Compound administered subcutaneously (S.C.), 1 and 5 hour post infection.

What is claimed is:

1. The compound of the formula

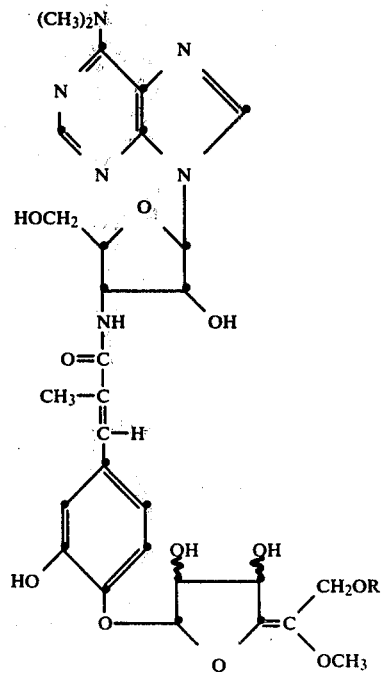

wherein R is
α-3,4-di-O-methylrhamnosyl.

2. The compound of the formula
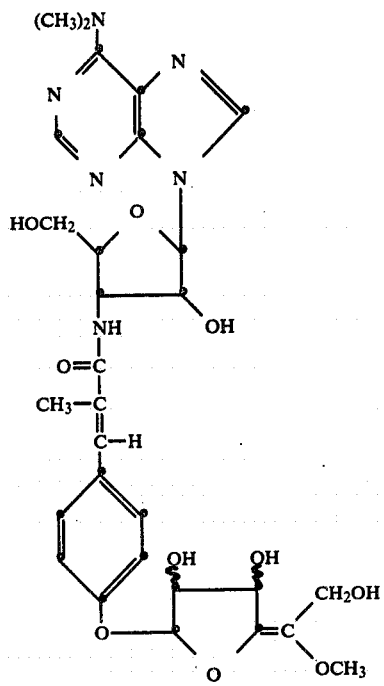
3. The compound of the formula
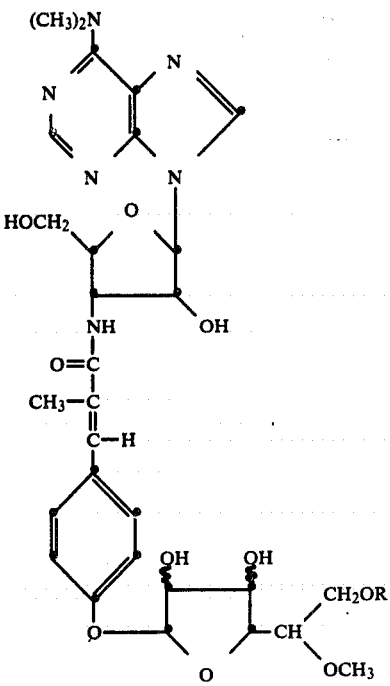
wherein R is
α-3,4-di-O-methylrhamnosyl.
* * * * *